(12) United States Patent
Smith et al.

(10) Patent No.: US 8,552,228 B2
(45) Date of Patent: Oct. 8, 2013

(54) PROCESS FOR THE PREPARATION OF 2,3,3,3-TETRAFLUOROPROPENE

(75) Inventors: John W. Smith, Cheshire (GB); Claire McGuiness, Cheshire (GB); Andrew P. Sharratt, Cheshire (GB)

(73) Assignee: Mexichem Amanco Holdings S.A. de C.V., Tlalnepantla (MX)

( * ) Notice: Subject to any disclaimer, the term of this patent is extended or adjusted under 35 U.S.C. 154(b) by 173 days.

(21) Appl. No.: 12/736,445

(22) PCT Filed: Apr. 9, 2009

(86) PCT No.: PCT/GB2009/000950
§ 371 (c)(1),
(2), (4) Date: Jan. 4, 2011

(87) PCT Pub. No.: WO2009/125201
PCT Pub. Date: Oct. 15, 2009

(65) Prior Publication Data
US 2011/0112340 A1 May 12, 2011

(30) Foreign Application Priority Data
Apr. 9, 2008 (GB) .................................. 0806389.3

(51) Int. Cl.
C07C 19/08 (2006.01)
(52) U.S. Cl.
USPC ............ 570/169; 570/156; 570/160; 570/165
(58) Field of Classification Search
None
See application file for complete search history.

(56) References Cited

U.S. PATENT DOCUMENTS

| | | | |
|---|---|---|---|
| 2,700,686 A | 1/1955 | Dickey | |
| 3,000,979 A | 11/1958 | Gibbs | |
| 2,889,379 A | 6/1959 | Ruh et al. | |
| 2,918,501 A | 12/1959 | Brehm et al. | |
| 2,931,840 A | 4/1960 | Marquis | |
| 2,996,555 A | 8/1961 | Rausch | |
| 3,398,204 A | 8/1968 | Gallant | |
| 3,674,665 A | 7/1972 | Cristol | |
| 3,739,036 A | 6/1973 | Valicenti | |
| 3,793,229 A | 2/1974 | Groppelli et al. | |
| 4,093,670 A | 6/1978 | Ozawa et al. | |
| 4,220,608 A | 9/1980 | Feiring | |
| 4,465,786 A | 8/1984 | Zimmer et al. | |
| 4,798,818 A | 1/1989 | Baizer | |
| 5,281,568 A * | 1/1994 | Scott et al. ................... | 502/307 |
| 5,679,875 A | 10/1997 | Aoyama et al. | |
| 5,811,603 A | 9/1998 | Elsheikh | |
| 6,111,150 A | 8/2000 | Sakyu et al. | |
| 6,329,559 B1 | 12/2001 | Sievert et al. | |
| 6,369,285 B1 | 4/2002 | Mathieu et al. | |
| 6,548,719 B1 | 4/2003 | Nair et al. | |
| 2005/0038302 A1 | 2/2005 | Hedrick | |
| 2006/0122441 A1 | 6/2006 | Tung | |
| 2007/0004585 A1 | 1/2007 | Amos | |
| 2007/0112230 A1 | 5/2007 | Mukhopadhyay | |
| 2007/0129579 A1 | 6/2007 | Wang | |
| 2007/0197842 A1 | 8/2007 | Mukhopadhyay | |

FOREIGN PATENT DOCUMENTS

| | | |
|---|---|---|
| DE | 1140928 | 12/1962 |
| DE | 2128341 | 12/1971 |
| EP | 0270006 | 6/1988 |
| EP | 0436989 | 7/1991 |
| EP | 0502605 | 9/1992 |
| EP | 0644173 | 3/1995 |
| EP | 0726243 | 8/1996 |
| EP | 0773061 | 5/1997 |
| EP | 0939071 | 9/1999 |
| EP | 957074 | 11/1999 |
| EP | 1350564 | 10/2003 |
| FR | 2342952 | 9/1977 |
| GB | 1407696 | 9/1975 |
| WO | WO 93/04025 | 3/1993 |
| WO | WO97/05089 | 2/1997 |
| WO | WO 98/10862 | 3/1998 |
| WO | WO 98/33756 | 8/1998 |
| WO | WO 98/37043 | 8/1998 |
| WO | WO99/62857 | 12/1999 |
| WO | WO2005/012212 | 2/2005 |
| WO | WO2005/023984 | 3/2005 |
| WO | WO 2005/037431 | 4/2005 |
| WO | WO2005/037743 | 4/2005 |
| WO | WO2005/037744 | 4/2005 |
| WO | WO2005/108334 | 11/2005 |
| WO | WO 2006/106353 | 10/2006 |
| WO | WO2007/019355 | 2/2007 |
| WO | WO2007/056128 | 5/2007 |
| WO | WO 2007/056194 | 5/2007 |

(Continued)

OTHER PUBLICATIONS

International Preliminary Report on Patentability and Written Opinion dated Oct. 12, 2010 in International Application No. PCT/GB2009/000950.
Banks R.E. et al; Preparation of 2,3,3,3-Tetrafluoropropene from Trifluoroacetylacetone and Sulphur Tetrafluoride; Fluoride Chem. (82), 1997; pp. 171-174.
Büchner; M. et al; Reactions of Gaseous; Halogenated Propene, Radical Cations with Ammonia: A Study of the . . . ; Chemistry: A European Journal, 1998, pp. 1799-1809, vol. 4.
Burton, D.J. et al; Preparation of E-1,2,3,3,3,-Pentafluoropropene, Z-1,2,3,3,3-Pentafluoropropene and E-1 . . . ; Journal of Fluorine Chemistry, 1989, pp. 167-174.
Haszeldine, R.N.; Fluoro-olefins. Part II: Synthesis and Reactions of Some 3,3,3-Trihalogenopropenes; J. Chem, Soc., 1953, pp. 3371-3378.
Joyce, R.M. et al; Free Radical-initiated Reaction of Ethylene with Carbon Tetrachloride; J. Am, Chem. Soc., 1948, pp. 2529-2532.
Smith, M.B. et al; March's Advanced Organic Chemistry: Reactions, Mechanisms and Structure; Advanced Organic Chemistry; 5th Edition, 2001, p. 1195.

(Continued)

Primary Examiner — Sudhakar Katakam
(74) Attorney, Agent, or Firm — Ryan Kromholz & Manion, S.C.

(57) ABSTRACT

The invention provides a process for the preparation of 2,3,3-tetrafluoropropene (1234yf) comprising (a) contacting 1,1,1-trifluoro-2,3-difluoropropane (243db) with hydrogen fluoride (HF) in the presence of a zinc/chromia catalyst to produce a compound having the formula $CF_3CHFCH_2X$, wherein X is Cl or F, and (b) dehydrohalogenating the compound of formula $CF_3CHFCH_2X$ to produce 1234yf.

22 Claims, No Drawings

(56) References Cited

FOREIGN PATENT DOCUMENTS

| WO | WO 2007/079431 | 7/2007 |
|----|----------------|--------|
| WO | WO 2008/030443 | 3/2008 |
| WO | WO 2008/040969 | 4/2008 |
| WO | WO 2008/054781 | 5/2008 |
| WO | WO 2008/054782 | 5/2008 |
| WO | WO 2008/075017 | 6/2008 |
| WO | WO2009/140563  | 11/2009 |

OTHER PUBLICATIONS

International Preliminary Report on Patentability for International Application No. PCT/GB2009/000950 dated Oct. 12, 2010.

Haszeldine et al., Fluoro-olefin Chemistry. Part X. SOme Additions to 1-Fluoropropene Under Ionic and Free-radical Conditions, J Chem. Soc Perkins Trans. 1 1976, pp. 2349-2353.

Meyer et al., Asymmetiric Cyclopropanation of Vinyl Fluorides: Acess to Enantiopure Monofluorinated Cyclopropane Carboxylates, Synthesis, 2000, pp. 1479-1490.

Boche et al., Sterospezifische Darstellung der (Z)-bxa. (e)-Isomeren von einigen Vinylfluoriden, Chem Ber., 1981, pp. 4005-4009 English Abstract.

Haszeldine et al., Additon of Free Radicals to Unsaturated Systems. Part XXI . . . , J. Chem. Soc. Perkin Trans. 1, 1974, pp. 1303-1307.

Haszeldine et al., Carbene Chemistry Part 11 Insertion Reactions of 1,2,2-Trifluoroethylidene into Carbon-Hydrogen Bonds . . . , J. Chem. Soc. Perkin Trans. 1, 1979 pp. 1943-1947.

Atherton et al., Carbene Chemistry Part II Migration in Fluoralkylcarbenes, J. Chem. Soc. 1971, pp. 366-371.

Baklouti et al., Synthese D'ethyleniques Monofluores, J. Fluorine Chem., 1981, pp. 181-190 (English Abstract).

Haszeldine et al., Free-radical Additions to Unsaturated Systems Part XVII Reaction of Trifluoroiodemethane with Mixtures of Ethylene . . . , J. Chem. Soc., 1970, pp. 414-421.

Haszeldine, Journal of the Society of Chemistry, 1951, pp. 2495-2504.

\* cited by examiner

PROCESS FOR THE PREPARATION OF 2,3,3,3-TETRAFLUOROPROPENE

The invention relates to a process for preparing 2,3,3,3-tetrafluoropropene. In particular, the invention relates to a process for preparing 2,3,3,3-tetrafluoropropene comprising fluorinating 1,1,1-trifluoro-2,3-dichloropropane and dehydrohalogenating a compound formed from the fluorination to produce 2,3,3,3-tetrafluoropropene.

2,3,3,3-tetrafluoropropene is also known as HFO-1234yf, HFC-1234yf or simply 1234yf. Hereinafter, unless otherwise stated, 2,3,3,3-tetrafluoropropene will be referred to as 1234yf. The known processes for preparing 1234yf typically suffer from disadvantages such as low yields, and/or the handling of toxic and/or expensive reagents, and/or the use of extreme conditions, and/or the production of toxic by-products. Methods for the preparation of 1234yf have been described in, for example, Journal Fluorine Chemistry (82), 1997, 171-174. In this paper, 1234yf is prepared by the reaction of sulphur tetrafluoride with trifluoroacetylacetone. However, this method is only of academic interest because of the hazards involved in handling the reagents and their expense. Another method for the preparation of 1234yf is described in U.S. Pat. No. 2,931,840. In this case, pyrolysis of C1 chlorofluorocarbons with or without tetrafluoroethylene was purported to yield 1234yf. However, the yields described were very low and again it was necessary to handle hazardous chemicals under extreme conditions. It would also be expected that such a process would produce a variety of very toxic by-products. In addition to addressing the disadvantages of the known methods, it would be desirable to provide a new method for the preparation of 1234yf that use only readily available feedstocks.

The listing or discussion of a prior-published document in this specification should not necessarily be taken as an acknowledgement that the document is part of the state of the art or is common general knowledge.

The present invention addresses the foregoing deficiencies of the known routes for preparing 1234yf by providing a process for its preparation comprising (a) contacting 1,1,1-trifluoro-2,3-dichloropropane with hydrogen fluoride (HF) in the presence of a zinc/chromia catalyst to produce a compound having the formula $CF_3CHFCH_2X$, wherein X is Cl or F; and (b) dehydrohalogenating the compound of formula $CF_3CHFCH_2X$ to produce 1234yf.

1,1,1-trifluoro-2,3-dichloropropane is also known as HCFC-243db or simply 243db. Hereinafter, unless otherwise stated, 1,1,1-trifluoro-2,3-dichloropropane will be referred to as 243db. For the avoidance of doubt, a compound of formula $CF_3CHFCH_2X$ (wherein X=Cl or F) may be either 1,1,1,2,3-pentafluoropropane (X=F, also known as HFC 245eb or just 245eb) or 1,1,1,2-tetrafluoro-3-chloropropane (X=Cl, also known as HFC 244eb or just 244eb), or a combination thereof.

Unless otherwise stated, as used herein, by the term "dehydrohalogenation" (or dehydrohalogenating), we refer to the removal of hydrogen chloride (HCl) or hydrogen fluoride (HF) from the compound of formula $CF_3CHFCH_2X$. Thus the term "dehydrohalogenation" includes "dehydrofluorination" and "dehydrochlorination" of the compound of formula $CF_3CHFCH_2X$.

Step (a) of the process of the invention comprises contacting 243db with HF in the presence of a zinc/chromia catalyst to produce a compound having the formula $CF_3CHFCH_2X$, i.e. step (a) is a fluorination step. The fluorination may be carried out in the vapour and/or liquid phase and at a temperature of from about −70 to about 400° C. The process may be carried out at atmospheric, sub- or super-atmospheric pressure, preferably from about 0 to about 30 bara.

The catalyst in step (a) may be used in an amount of from about 0.01 to about 50% by weight, such as from about 0.1 to about 30%, for example from about 0.5 to about 20%, based on the combined weight of 243db and HF.

Step (b) of the process of the invention may be carried out by any suitable reactions conditions effective to dehydrohalogenate (i.e. dehydrochlorinate or dehydrofluorinate) the compound of formula $CF_3CHFCH_2X$ to produce 1234yf. Preferably, the dehydrohalogenation is carried out in the vapour and/or liquid phase and may be carried out at a temperature of from about −70 to about 1000° C. (e.g. about 0 to about 400° C.). The process may be carried out at atmospheric sub- or super atmospheric pressure, preferably from about 0 to about 30 bara.

The dehydrohalogenation may be induced thermally, may be base-mediated and/or may be catalysed by any suitable catalyst. Suitable catalysts include metal and carbon based catalysts such as those comprising activated carbon, main group (e.g. alumina-based catalysts) and transition metals, such as chromia-based catalysts (e.g. zinc/chromia) or nickel-based catalysts (e.g. nickel mesh).

One preferred method of effecting the dehydrohalogenation of the compound of formula $CF_3CHFCH_2X$ to produce 1234yf is by contacting $CF_3CHFCH_2X$ with a metal catalyst, such as a chromia-based (e.g. zinc/chromia) catalyst. Thus, steps (a) and (b) may be carried out in a "one-pot" manner, i.e. simultaneously. Alternatively, when both steps (a) and (b) are carried out in the presence of a metal catalyst, such as a chromia-based (e.g. zinc/chromia) catalyst, the fluorination and dehydrohalogenation reactions may be carried out in two discrete steps, for example using two or more discrete reaction zones or vessels.

Step (a) and/or step (b) can be carried out in any suitable apparatus, such as a static mixer, a stirred tank reactor or a stirred vapour-liquid disengagement vessel. Preferably, this or any other apparatus described herein is made from one or more materials that are resistant to corrosion, e.g. Hastelloy® or Inconel®. The process may be carried out batch-wise or continuously.

When both steps (a) and (b) are carried out in the presence of a zinc/chromia catalyst, the reaction conditions for each step (a) and (b) may be the same (e.g. in a one-pot process) or different. Preferably, the reaction conditions when steps (a) and (b) are carried out in the presence of a zinc/chromia catalyst can be selected to be different so as to optimise the fluorination and dehydrohalogenation reactions, respectively. This is explained in more detail below.

Fluorination step (a) preferably is conducted at a temperature of from about 0 to about 390° C., such as from about 100 to about 380° C. or from about 200 to about 370° C. (e.g. from about 240 to about 260° C.). When conducted in the presence of a zinc/chromia catalyst, step (b) preferably is conducted at a temperature of from about 200 to about 360° C., such as from about 240 to about 340° C.

It is currently considered to be advantageous to use a higher pressure in step (a) (to promote fluorination) than in step (b) (to promote dehydrohalogenation). Thus, step (a) preferably is carried out from about 5 to about 28 bara, such as from about 10 to about 25 bara (e.g. 15 to 20 bara), whereas step (b) preferably is carried out from about 0.01 to about 25 bara or about 0.1 to about 20 bara, such as from about 1 to about 10 bara (e.g. 1 to 5 bara).

Fluorination step (a) of the invention is carried out by contacting 243db with HF. Step (b) of the invention may be carried out in the presence of HF. For example residual HF from step (a) may be present, and/or HF from a separate feed. Alternatively, step (b) may be carried out in the absence of HF, for example following separation of the compound of formula $CF_3CHFCH_2X$ from HF prior to step (b), and with no additional co-feed of HF. In certain embodiments it may be desirable to use some HF in order to prevent and/or retard excessive decomposition of the organic feed and/or coking of the catalyst in step (b).

When both steps (a) and (b) are carried out in the presence of a zinc/chromia catalyst and HF, the molar ratio of HF:organics can be selected to be different in each step so as to promote fluorination in step (a) and dehydrohalogenation in step (b). For example, the molar ratio of HF:organics (e.g. 243db) in step (a) preferably is from about 1:1 to about 100:1, such as from about 2:1 to about 50:1, for example from about 5:1 to about 40:1 (e.g. from about 10:1 to about 30:1). For step (b), the molar ratio of HF:organics (e.g. the compound of formula $CF_3CHFCH_2X$) preferably is from about 0.01:1 to about 50:1, such as from about 0.1:1 to about 40:1, for example from about 0.5:1 to about 30:1 or about 2:1 to about 15:1 (e.g. from about 10:1 to about 20:1 or from about 5:1 to about 10:1).

Another way of increasing the concentration of HF in step (a) relative to step (b) (thereby facilitating the fluorination/dehydrohalogenation reactions in these steps) is by adding a diluent gas (e.g. nitrogen) to step (b).

Another preferred method of effecting the dehydrohalogenation of the compound of formula $CF_3CHFCH_2X$ to produce 1234yf is by contacting $CF_3CHFCH_2X$ with a base (base-mediated dehydrohalogenation).

This base-mediated dehydrohalogenation process of step (b) comprises contacting the $CF_3CHFCH_2X$ with base such as a metal hydroxide or amide (preferably a basic metal hydroxide or amide, e.g. an alkali or alkaline earth metal hydroxide or amide).

Unless otherwise stated, as used herein, by the term "alkali metal hydroxide", we refer to a compound or mixture of compounds selected from lithium hydroxide, sodium hydroxide, potassium hydroxide, rubidium hydroxide and caesium hydroxide. Similarly, by the term "alkali metal amide", we refer to a compound or mixture of compounds selected from lithium amide, sodium amide, potassium amide, rubidium amide and caesium amide.

Unless otherwise stated, as used herein, by the term "alkaline earth metal hydroxide", we refer to a compound or mixture of compounds selected from beryllium hydroxide, magnesium hydroxide, calcium hydroxide, strontium hydroxide and barium hydroxide. Similarly, by the term "alkaline earth metal amide", we refer to a compound or mixture of compounds selected from beryllium amide, magnesium amide, calcium amide, strontium amide and barium amide.

Typically, the base-mediated dehydrohalogenation process of step (b) is conducted at a temperature of from −50 to 300° C. Preferably, the process is conducted at a temperature of from 20 to 250° C., for example from 50 to 200° C. The base-mediated dehydrohalogenation may be conducted at a pressure of from 0 to 30 bara.

The reaction time for the base-mediated dehydrohalogenation process of step (b) may vary over a wide range. However, the reaction time will typically be in the region of from 0.01 to 100 hours, such as from 0.1 to 50 hours, e.g. from 1 to 20 hours.

Of course, the skilled person will appreciate that the preferred conditions (e.g. temperature, pressure and reaction time) for conducting the base-mediated dehydrohalogenation may vary depending on a number of factors such as the nature of the compound of formula $CF_3CHFCH_2X$, the base being employed, and/or the presence of a catalyst etc.

The base-mediated dehydrohalogenation process of step (b) may be carried out in the presence or absence of a solvent. If no solvent is used, the compound of formula $CF_3CHFCH_2X$ may be passed into or over molten base or hot base, for example in a tubular reactor. If a solvent is used, in some embodiments a preferred solvent is water, although many other solvents may be used. In some embodiments solvents such as alcohols (e.g. propan-1-ol), diols (e.g. ethylene glycol) and polyols such as polyethylene glycol (e.g. PEG200 or PEG300) may be preferred. These solvents can be used alone or in combination. In further embodiments, solvents from the class known as polar aprotic solvents may be preferred. Examples, of such polar aprotic solvents include diglyme, sulfolane, dimethylformamide (DMF), dioxane, acetonitrile, hexamethylphosphoramide (HMPA), dimethyl sulphoxide (DMSO) and N-methyl pyrrolidone (NMP). The boiling point of the solvent is preferably such that it does not generate excessive pressure under reaction conditions.

A preferred base is an alkali metal hydroxide selected from the group consisting of lithium hydroxide, sodium hydroxide and potassium hydroxide, more preferably, sodium hydroxide and potassium hydroxide and most preferably potassium hydroxide.

Another preferred base is an alkaline earth metal hydroxide selected from the group consisting of magnesium hydroxide and calcium hydroxide, more preferably calcium hydroxide.

The base is typically present in an amount of from 1 to 50 weight % based on the total weight of the components which make up step (b). Preferably, the base is present in an amount of from 5 to 30 weight %.

The molar ratio of base to compound of formula $CF_3CHFCH_2X$ is typically from 1:20 to 50:1, preferably from 1:5 to 20:1, for example from 1:2 to 10:1.

As mentioned above, the base-mediated dehydrohalogenation may preferably employ water as the solvent. Thus, the dehydrohalogenation reaction may preferably use an aqueous solution of at least one base, such as an alkali (or alkaline earth) metal hydroxide, without the need for a co-solvent or diluent. However, a co-solvent or diluent can be used for example to modify the system viscosity, to act as a preferred phase for reaction by-products, or to increase thermal mass. Useful co-solvents or diluents include those that are not reactive with or negatively impact the equilibrium or kinetics of the process and include alcohols such as methanol and ethanol; diols such as ethylene glycol; ethers such as diethyl ether, dibutyl ether; esters such as methyl acetate, ethyl acetate and the like; linear, branched and cyclic alkanes such as cyclohexane, methylcyclohexane; fluorinated diluents such as hexafluoroisopropanol, perfluorotetrahydrofuran and perfluorodecalin.

The base-mediated dehydrohalogenation of step (b) is preferably conducted in the presence of a catalyst. The catalyst is preferably a phase transfer catalyst which facilitates the transfer of ionic compounds into an organic phase from, for example, a water phase. If water is used as a solvent, an aqueous or inorganic phase is present as a consequence of the alkali metal hydroxide and an organic phase is present as a result of the fluorocarbon. The phase transfer catalyst facilitates the reaction of these dissimilar components. While various phase transfer catalysts may function in different ways, their mechanism of action is not determinative of their utility in the present invention provided that they facilitate the dehydrohalogenation reaction. The phase transfer catalyst can be ionic or neutral and is typically selected from the group consisting of crown ethers, onium salts, cryptands and polyalkylene glycols and derivatives thereof (e.g. fluorinated derivatives thereof).

An effective amount of the phase transfer catalyst should be used in order to effect the desired reaction, influence selectivity to the desired products or enhance the yield; such an amount can be determined by limited experimentation once the reactants, process conditions and phase transfer catalyst are selected. Typically, the amount of catalyst used relative to the amount of compound of formula $CF_3CHFCH_2X$ present is from 0.001 to 20 mol %, such as from 0.01 to 10 mol %, e.g. from 0.05 to 5 mol %.

Crown ethers are cyclic molecules in which ether groups are connected by dimethylene linkages. Crown ethers form a molecular structure that is believed to be capable of receiving or holding the alkali metal ion of the hydroxide and to thereby facilitate the reaction. Particularly useful crown ethers include 18-crown-6 (especially in combination with potassium hydroxide), 15-crown-5 (especially in combination with sodium hydroxide) and 12-crown-4 (especially in combination with lithium hydroxide).

Derivatives of the above crown ethers are also useful, such as dibenzyl-18-crown-6, dicyclohexanyl-18-crown-6, dibenzyl-24-crown-8 and dibenzyl-12-crown-4. Other compounds analogous to the crown ethers and useful for the same purpose are compounds which differ by the replacement of one or more of the oxygen atoms by other kinds of donor atoms, particularly N or S. Fluorinated derivatives of all the above may also be used.

Cryptands are another class of compounds useful in the base-mediated dehydrohalogenation as phase transfer catalysts. These are three dimensional polymacrocyclic chelating agents that are formed by joining bridgehead structures with chains that contain properly spaced donor atoms. The donor atoms of the bridges may all be O, N, or S, or the compounds may be mixed donor macrocycles in which the bridge strands contain combinations of such donor atoms. Suitable cryptands include bicyclic molecules that result from joining nitrogen bridgeheads with chains of ($-OCH_2CH_2-$) groups, for example as in [2.2.2]cryptand (4,7,13,16,21,24-hexaoxa-1,10-diazabicyclo[8.8.8]hexacosane, available under the brand names Kryptand 222 and Kryptofix 222).

Onium salts that may be used as catalysts in the base-mediated process of the step (b) include quaternary phosphonium salts and quaternary ammonium salts, which may be represented by the formulae $R^1R^2R^3R^4P^+Z^-$ and $R^1R^2R^3R^4N^+Z^-$, respectively. In these formulae, each of $R^1$, $R^2$, $R^3$ and $R^4$ typically represent, independently, a $C_{1-10}$ alkyl group, an aryl group (e.g. phenyl, naphthyl or pyridinyl) or an arylalkyl group (e.g. benzyl or $C_{1-10}$ alkyl-substituted phenyl), and $Z^-$ is a halide or other suitable counterion (e.g. hydrogen sulphate).

Specific examples of such phosphonium salts and quaternary ammonium salts include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulphate, tetra-n-butylphosphonium chloride, tetraphenylphosphonium bromide, tetraphenylphosphonium chloride, triphenylmethylphosphonium bromide and triphenylmethylphosphonium chloride. Benzyltriethylammonium chloride is preferred for use under strongly basic conditions.

Other useful onium salts include those exhibiting high temperature stabilities (e.g. up to about 200° C.), for example 4-dialkylaminopyridinium salts, tetraphenylarsonium chloride, bis[tris(dimethylamino)phosphine]iminium chloride and tetrakis[tris(dimethylamino)phosphinimino]phosphonium chloride. The latter two compounds are also reported to be stable in the presence of hot, concentrated sodium hydroxide and, therefore, can be particularly useful.

Polyalkylene glycol compounds useful as phase transfer catalysts may be represented by the formula $R^6O(R^5O)_mR^7$ wherein $R^5$ is a $C_{1-10}$ alkylene group, each of $R^6$ and $R^7$ are, independently, H, a $C_{1-10}$ alkyl group, an aryl group (e.g. phenyl, naphthyl or pyridinyl) or an arylalkyl group (e.g. benzyl or $C_{1-10}$ alkyl-substituted phenyl), and m is an integer of at least 2. Preferable both $R^6$ and $R^7$ are the same, for example they may both by H.

Such polyalkylene glycols include diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, monoalkyl glycol ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers of such glycols, and polyalkylene glycols such as polyethylene glycol (average molecular weight about 300) and polyethylene glycol (average molecular weight about 400) and the dialkyl (e.g. dimethyl, dipropyl, dibutyl)ethers of such polyalkylene glycols.

Combinations of phase transfer catalysts from within one of the groups described above may also be useful as well as combinations or mixtures from more than one group. Crown ethers and quaternary ammonium salts are the currently preferred groups of catalysts, for example 18-crown-6 and its fluorinated derivatives and benzyltriethylammonium chloride.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074 and WO 98/10862, which are incorporated by reference herein. However, the present inventors have surprisingly found that zinc/chromia catalysts may be used promote the fluorination of 243db to produce the compound of formula $CF_3CHFCH_2X$ and, optionally, to promote the dehydrohalogenation of the compound of formula $CF_3CHFCH_2X$ to produce 1234yf. The combined fluorination/dehydrohalogenation to produce 1234yf starting from 243db in the presence of a zinc/chromia catalyst is particularly unexpected.

Typically, the chromium or compound of chromium present in the zinc/chromia catalysts of the invention is an oxide, oxyfluoride or fluoride of chromium such as chromium oxide.

The total amount of the zinc or a compound of zinc present in the zinc/chromia catalysts of the invention is typically from about 0.01% to about 25%, preferably 0.1% to about 25%, conveniently 0.01% to 6% zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst.

In other embodiments, the catalyst conveniently comprises 0.01% to 1%, more preferably 0.05% to 0.5% zinc.

The preferred amount depends upon a number of factors such as the nature of the chromium or a compound of chromium and/or zinc or a compound of zinc and/or the way in which the catalyst is made. These factors are described in more detail hereinafter.

It is to be understood that the amount of zinc or a compound of zinc quoted herein refers to the amount of elemental zinc, whether present as elemental zinc or as a compound of zinc.

The zinc/chromia catalysts used in the invention may include an additional metal or compound thereof. Typically, the additional metal is a divalent or trivalent metal, preferably selected from nickel, magnesium, aluminium and mixtures thereof. Typically, the additional metal is present in an amount of from 0.01% by weight to about 25% by weight of the catalyst, preferably from about 0.01 to 10% by weight of the catalyst. Other embodiments may comprise at least about 0.5% by weight or at least about 1% weight of additional metal.

The zinc/chromia catalysts used in the present invention may be amorphous. By this we mean that the catalyst does not demonstrate substantial crystalline characteristics when analysed by, for example, X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

During use in a fluorination/dehydrohalogenation reaction the degree of crystallinity may change. Thus it is possible that a catalyst of the invention that has a degree of crystallinity as defined above before use in a fluorination/dehydrohalogenation reaction and will have a degree of crystallinity outside these ranges during or after use in a fluorination/dehydrohalogenation reaction.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (eg the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The zinc/chromia catalysts of the invention typically have a surface area of at least 50 $m^2/g$ and preferably from 70 to 250 $m^2/g$ and most preferably from 100 to 200 $m^2/g$ before it is subjected to pre-treatment with a fluoride containing species such as hydrogen fluoride or a fluorinated hydrocarbon. During this pre-treatment, which is described in more detail hereinafter, at least some of the oxygen atoms in the catalyst are replaced by fluorine atoms.

The zinc/chromia catalysts of the invention typically have an advantageous balance of levels of activity and selectivity. Preferably, they also have a degree of chemical robustness that means that they have a relatively long working lifetime. The catalysts of the invention preferably also have a mechanical strength that enables relatively easy handling, for example they may be charged to reactors or discharged from reactors using known techniques.

The zinc/chromia catalysts of the invention may be provided in any suitable form known in the art. For example, they may be provided in the form of pellets or granules of appropriate size for use in a fixed bed or a fluidised bed. The catalysts may be supported or unsupported. If the catalyst is supported, suitable supports include $AlF_3$, fluorinated alumina or activated carbon.

The zinc/chromia catalysts of the invention include promoted forms of such catalysts, including those containing enhanced Lewis and/or Brönsted acidity and/or basicity.

The amorphous catalysts which may be used in the present invention can be obtained by any method known in the art for producing amorphous chromia-based catalysts. Suitable methods include co-precipitation from solutions of zinc and chromium nitrates on the addition of ammonium hydroxide. Alternatively, surface impregnation of the zinc or a compound thereof onto an amorphous chromia catalyst can be used.

Further methods for preparing the amorphous zinc/chromia catalysts include, for example, reduction of a chromium (VI) compound, for example a chromate, dichromate, in particular ammonium dichromate, to chromium (III), by zinc metal, followed by co-precipitation and washing; or mixing as solids, a chromium (VI) compound and a compound of zinc, for example zinc acetate or zinc oxalate, and heating the mixture to high temperature in order to effect reduction of the chromium (VI) compound to chromium (III) oxide and oxidise the compound of zinc to zinc oxide.

The zinc may be introduced into and/or onto the amorphous chromia catalyst in the form of a compound, for example a halide, oxyhalide, oxide or hydroxide depending at least to some extent upon the catalyst preparation technique employed. In the case where amorphous catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of zinc and chromium may be co-precipitated (for example by the use of a base such as sodium hydroxide or ammonium hydroxide) and then converted to the oxides to prepare the amorphous catalyst. Mixing and milling of an insoluble zinc compound with the basic chromia catalyst provides a further method of preparing the amorphous catalyst precursor. A method for making amorphous catalyst based on chromium oxyhalide comprises adding a compound of zinc to hydrated chromium halide.

The amount of zinc or a compound of zinc introduced to the amorphous catalyst precursor depends upon the preparation method employed. It is believed that the working catalyst has a surface containing cations of zinc located in a chromium-containing lattice, for example chromium oxide, oxyhalide, or halide lattice. Thus the amount of zinc or a compound of zinc required is generally lower for catalysts made by impregnation than for catalysts made by other methods such as co-precipitation, which also contain the zinc or a compound of zinc in non-surface locations.

Any of the aforementioned methods, or other methods, may be employed for the preparation of the amorphous catalysts which may be used in the process of the present invention.

The zinc/chromia catalysts described herein are typically stabilised by heat treatment before use such that they are stable under the environmental conditions that they are exposed to in use. This stabilisation is often a two-stage process. In the first stage, the catalyst is stabilised by heat treatment in nitrogen or a nitrogen/air environment. In the art, this stage is often called "calcination". Fluorination catalysts are then typically stabilised to hydrogen fluoride by heat treatment in hydrogen fluoride. This stage is often termed "pre-fluorination".

By careful control of the conditions under which these two heat treatment stages are conducted, crystallinity can be induced into the catalyst to a controlled degree.

For example, an amorphous catalyst may be heat treated at a temperature of from about 300 to about 600° C., preferably from about 400 to 600° C., more preferably from 500 to 590° C., for example 520, 540, 560 or 580° C. for a period of from about 1 to about 12 hours, preferably for from about 2 to about 8 hours, for example about 4 hours in a suitable atmosphere. Suitable atmospheres under which this heat treatment can be conducted include an atmosphere of nitrogen or an atmosphere having an oxygen level of from about 0.1 to about 10% v/v in nitrogen. Other oxidizing environments could alternatively be used. For example, environments containing suitable oxidizing agents include, but are not limited to, those containing a source of nitrate, $CrO_3$ or $O_2$ (for example air). This heat treatment stage can be conducted in addition to or instead of the calcining stage that is typically used in the prior art to produce amorphous catalysts.

Conditions for the pre-fluorination stage can be selected so that they do not substantially introduce crystallinity into the catalyst. This may be achieved by heat treatment of the catalyst precursor at a temperature of from about 200 to about 500° C., preferably from about 250 to about 400° C. at atmospheric or super atmospheric pressure for a period of from about 1 to about 16 hours in the presence of hydrogen fluoride, optionally in the presence of another gas such as nitrogen.

Conditions for the pre-fluorination stage can be selected so that they induce a change in the crystallinity of the catalyst or so that they do not induce such a change. The present inventors have found that heat treatment of the catalyst precursor at a temperature of from about 250 to about 500° C., preferably from about 300 to about 400° C. at atmospheric or super atmospheric pressure for a period of from about 1 to about 16 hours in the presence of hydrogen fluoride, optionally in the presence of another gas such as air, can produce a catalyst in which the crystallinity is as defined above, for example from 0.1 to 8.0% by weight of the catalyst (typically from 0.1 to less than 8.0% by weight of the catalyst) is in the form of one or more crystalline compounds of chromium and/or one or more crystalline compounds of the at least one additional metal.

The skilled person will appreciate that by varying the conditions described above, such as by varying the temperature and/or time and/or atmosphere under which the heat treatment is conducted, the degree of crystallinity of the catalyst may be varied. Typically, for example, catalysts with higher degrees of crystallinity (e.g. from 8 to 50% by weight of the catalyst) may be prepared by increasing the temperature and/or increasing the calcination time and/or increasing the oxidising nature of the atmosphere under which the catalyst pre-treatment is conducted.

The variation of catalyst crystallinity as a function of calcination temperature, time and atmosphere is illustrated by the following table showing a series of experiments in which 8 g samples of a 6% zinc/chromia catalyst were subjected to calcination across a range of conditions and the level of crystallinity induced determined by X-Ray diffraction.

| Calcination Time (t, hrs) | Calcination Temperature (T, ° C.) | Atmosphere nitrogen:air (D, v/v) | % Cryst $Cr_2O_3$ Content |
|---|---|---|---|
| 4 | 400.0 | 15 | 1 |
| 4 | 400.0 | 15 | 1 |
| 2 | 450.0 | 20 | 9 |
| 6 | 350.0 | 20 | 0 |
| 2 | 450.0 | 10 | 18 |
| 2 | 350.0 | 10 | 0 |
| 6 | 450.0 | 20 | 20 |
| 6 | 350.0 | 10 | 0 |
| 6 | 450.0 | 10 | 30 |
| 4 | 400.0 | 15 | 1 |
| 2 | 350.0 | 20 | 0 |

The pre-fluorination treatment typically has the effect of lowering the surface area of the catalyst. After the pre-fluorination treatment the catalysts of the invention typically have a surface area of 20 to 200 $m^2/g$, such as 50 to 150 $m^2/g$, for example less than about 100 $m^2/g$.

In use, the zinc/chromia catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst. Alternatively, the catalyst can be regenerated continuously whilst in use by introducing an oxidising gas into the reactor e.g. oxygen or chlorine.

1,1,1-trifluoro-2,3-dichloropropane (243db) is commercially available (e.g. from Apollo Scientific Ltd, UK). Alternatively, 243db may also be prepared via a synthetic route starting from the cheap feedstocks carbon tetrachloride ($CCl_4$) and ethylene (see the reaction scheme set out below). These two starting materials may be telomerised to produce 1,1,1,3-tetrachloropropane (see, for example, J. Am. Chem. Soc. Vol. 70, p 2529, 1948, which is incorporated herein by reference) (also known as HCC-250fb, or simply 250fb).

250fb may then be fluorinated to produce 3,3,3-trifluoropropene (1243zf) and/or 1,1,1-trifluoro-3-chloropropane (e.g. using HF, optionally in the presence of a chromia-containing catalyst, preferably a zinc/chromia catalyst as described herein). Dehydrohalogenation of 1,1,1-trifluoro-3-chloropropane (e.g. using NaOH or KOH) produces 3,3,3-trifluoropropene (1243zf). Alternatively, 250fb may be dehydrochlorinated to 3,3,3-trichloropropene, followed by fluorination to 1243zf.

1243zf may then be readily halogenated, such as chlorinated (e.g. with chlorine) to produce 1,1,1-trifluoro-2,3-dichloropropane (243db). This reaction scheme is summarised below (minus the route from 250fb to 1243zf via 3,3,3-trichloropropene).

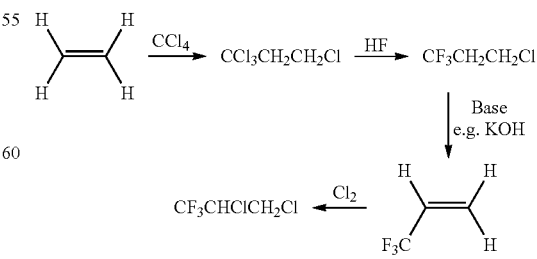

Thus, in another aspect of the invention, there is provided a process for preparing 1234yf, the process comprising:

(i) telomerising ethylene and carbon tetrachloride (CCl$_4$) to produce 1,1,1,3-tetrachloropropane (250fb);
(ii) converting 250fb to 3,3,3-trifluoropropene (1243zf);
(iii) contacting 1243zf with a compound of formula AB to produce a compound of formula CF$_3$CHACH$_2$B, wherein A and B represent, independently, H, F, Cl, Br or I, provided that A and B are not both H or F;
(iv) contacting the compound of formula CF$_3$CHACH$_2$B with hydrogen fluoride (HF) in the presence of a zinc/chromia catalyst to produce a compound having the formula CF$_3$CHFCH$_2$X, wherein X is Cl or F; and
(v) dehydrohalogenating the compound of formula CF$_3$CHFCH$_2$X to produce 1234yf.

Step (i) of the above process typically comprises contacting ethylene with CCl$_4$ in the liquid and/or vapour phase in presence of a catalyst under conditions suitable to produce 250fb.

Any suitable catalyst may be used in step (i), such as a catalyst which comprises iron, copper and/or peroxide.

Catalysts which comprise peroxide include benzoyl peroxide and di-t-butyl peroxide. Catalysts which comprise iron include iron powder and ferric/ferrous halides (e.g. chlorides). Catalysts which comprise copper include salts of copper such as copper halides (e.g. CuCl$_2$), copper sulphate and/or copper cyanide.

Typically, the catalysts which comprise copper and iron are used with a co-catalyst or ligand. Suitable co-catalysts include triethylorthoformate (HC(OEt)$_3$), nitrogen/phosphorus-containing ligands, and/or ammonium/phosphonium salts. Preferred nitrogen-containing ligands include amines (e.g. primary and secondary amines), nitriles and amides. Preferred phosphorus containing ligands include phosphates, phosphites (e.g. triethylphosphite) and phosphines. Preferred ammonium and phosphonium salts include ammonium and phosphonium halides (e.g. chlorides).

The catalyst for step (i) typically is used in an amount from about 0.01 to about 50 mol % (e.g. about 0.1 to about 10%), based on the molar sum of CCl$_4$ and ethylene present. An excess of the carbon tetrachloride over ethylene generally is used. For example, the molar ratio of CCl$_4$:C$_2$H$_4$ typically is from about 1:1 to about 50:1, such as from about 1.1:1 to about 20:1, for example from about 1.2:1 to about 10:1 or about 1.5:1 to about 5:1.

The reaction temperature for step (i) typically is within the range of from about 20 to about 300° C., preferably from about 30 to about 250° C., such as from about 40 to about 200° C., e.g. from about 50 to about 150° C.

The reaction pressure for step (i) typically is within the range of from 0 to about 40 bara, preferably from about 1 to about 30 bara.

The reaction time for step (i) generally is from about 1 second to about 100 hours, preferably from about 10 seconds to about 50 hours, such as from about 1 minute to about 10 hours.

Step (i) can be carried out in any suitable apparatus, such as a static mixer, a tubular reactor, a stirred tank reactor or a stirred vapour-liquid disengagement vessel. Step (i) may be carried out batch-wise or continuously. Preferably, the 1,1,1,3-tetrachloropropane formed in step (i) is purified and/or isolated before it is fluorinated in step (ii). The purification may be achieved by separation of the 250fb from any other products or reagents by one or more distillation, condensation or phase separation steps and/or by scrubbing with water or aqueous base.

The conversion of 250fb to 1243zf in step (ii) above typically involves fluorination and dehydrohalogenation substeps.

For example, 250fb may be fluorinated to produce a compound of formula CF$_3$CH$_2$CH$_2$Cl (253fb), followed by dehydrohalogenation of 253fb to produce 1243zf. This will be referred to hereinafter as route (ii1).

Alternatively, 250fb may be dehydrochlorinated to produce 3,3,3-trichloropropene, followed by fluorination to produce 1243zf. This will be referred to hereinafter as route (ii2).

Either or both routes (ii1) and (ii2) may be used to convert 250fb to 1243zf, depending on the choice of reagents and/or catalysts. The route taken and the number of steps involved may depend on factors such as the reaction conditions and the nature of catalyst employed (if any). Such factors are described in more detail below.

In route (ii1), for example, 250fb may be fluorinated with HF in the presence of a catalyst to produce 253fb. Any suitable catalyst for HF fluorination may be used, such as compounds comprising aluminium (e.g. alumina-based catalysts) and/or chromium (e.g. chromia-based catalysts, especially zinc/chromia catalysts as described herein) and/or metal halides such as chlorides or fluorides (e.g. TaX$_5$, SbX$_5$, SnX$_4$, TiX$_4$, FeCl$_3$, NbX$_5$, VX$_5$, AlX$_3$, wherein X=F or Cl) and/or nitrogen-containing bases (e.g. amines and nitrogen-containing heterocycles such as pyridine). Examples of catalysts compounds comprising aluminium include AlF$_3$, optionally mixed with one or more transition metal compounds.

253fb may then be dehydrohalogenated to 1243zf by any suitable method, for example by base-mediated (e.g. using a base comprising alkali or alkaline earth metal hydroxides or amides), thermal or metal catalysed (e.g. zinc/chromia catalysed) dehydrohalogenation. The dehydrohalogenation may be conducted in the presence or absence of HF. Suitable reaction conditions for the dehydrohalogenation of 253fb are described hereinbefore in relation to the dehydrohalogenation step (b) of a compound of formula CF$_3$CHFCH$_2$X (wherein X=Cl or F).

The fluorination and dehydrohalogenation reactions in route (ii1) using HF may be conducted simultaneously (i.e. in a one-pot process) or sequentially, optionally with separation/isolation of the 253fb prior to dehydrohalogenation. Preferably, route (ii1) is carried out in one-pot using a zinc/chromia catalyst.

In route (ii2), the dehydrochlorination and fluorination reactions may be carried out under substantially the same reaction conditions, i.e. in a one-pot process. Thus, 250fb may be contacted with HF in the presence of a catalyst to produce 1243zf, typically via 253fb. Suitable catalysts include the catalysts described above in relation to route (ii1), particularly zinc/chromia catalysts.

Although HF is described as a suitable fluorination agent for step (ii), any suitable fluorination agent may be used. For example, in an alternative embodiment, 3,3,3-trifluoropropene may be produced in one pot by treating 1,1,1,3-tetrachloropropane with NaF, KF, or amine:HF complexes such as Olah's reagent.

Typically, step (ii) is carried out at a temperature of about 20 to about 500° C. For example, when using KF or Olah's reagent (pyrindinium poly(HF)), temperatures of about 50 to about 200° C. may be used. Alternatively, when using HF, higher temperatures may be employed, such as from about 100 to about 500° C. (e.g. about 120 to about 400° C. or about 150 to about 250° C.).

The temperature used may vary depending on the nature of the catalyst employed. For example, when a nitrogen-containing base is used, the preferred temperature may range from about 100 to about 250° C., whereas when a catalyst based on a compound of aluminium is employed, the preferred temperature may vary from about 200 to about 350° C.

When a zinc/chromia catalyst is used for step (ii), the temperature typically ranges from about 150 to about 400° C., such as from about 150 to about 350° C., e.g. from about 150 to about 300° C. or from about 150 to about 250° C.

The reaction pressure for step (ii) typically is within the range of from 0 to about 30 bara, preferably from about 1 to about 20 bara.

An excess of the fluorination agent is generally used in step (ii), whether the 3,3,3-trifluoropropene is produced via route (ii1) or route (ii2). For example, when using HF as the fluorination agent, a molar ratio of HF:organics of from about 1:1 to about 100:1, such as from about 3:1 to about 50:1, e.g. from about 6:1 to about 30:1 may be used.

The reaction time for step (ii) generally is from about 1 second to about 100 hours, preferably from about 10 seconds to about 50 hours, such as from about 1 minute to about 10 hours. In a continuous process, typical contact times of the catalyst with the reagents is from about 1 to about 1000 seconds, such from about 1 to about 500 seconds or about 1 to about 300 seconds or about 1 to about 50, 100 or 200 seconds.

Step (ii) can be carried out in any suitable apparatus, such as a static mixer, a tubular reactor, a stirred tank reactor or a stirred vapour-liquid disengagement vessel. Step (ii) may be carried out batch-wise or continuously. Preferably, the 1243zf formed in step (ii) is purified and/or isolated before it is reacted in step (iii). The purification may be achieved by separation of the 1243zf from any other products or reagents by one or more distillation, condensation or phase separation steps and/or by scrubbing with water or aqueous base.

Step (ii) is described in more detail towards the end of this specification in a further embodiment denoted the 1243zf preparation process.

Step (iii) is the halogenation of 1243zf and comprises contacting 1243zf with a compound of formula AB to produce a compound of formula $CF_3CHACH_2B$, wherein A and B represent, independently, H, F, Cl, Br or I, provided that A and B are not both H or F. Any suitable halogenating agent AB may be used in step (iii) to convert 1243zf to the compound of formula $CF_3CHACH_2B$. Examples include $Cl_2$, $Br_2$, $I_2$, ClF, ClBr, and ICl, each optionally in the presence of HF. Preferably, at least one of A or B is Cl and, therefore, 1243zf may be chlorinated by contacting it with $Cl_2$, ClF, ClBr and/or ICl. Chlorine ($Cl_2$) is a preferred chlorinating agent. Preferably, step (iii) is carried out by contacting 1243zf with chlorine ($Cl_2$) to produce 243db.

Step (iii) is advantageously carried out in the presence of a catalyst. Any suitable catalyst may be used, including catalysts comprising a transition metal (e.g. Ti, V, Cr, Mn, Fe, Co, Ni, Sn, Ta, Sb, Au, Ag, Mo, Ru, Rh, Pd, Pt or compounds thereof or mixtures of the foregoing) or a main group element such as carbon, silicon or aluminium or compounds thereof or mixtures of the foregoing. A preferred group of chlorination catalysts are those comprising activated carbon, alumina and/or an oxide of a transition metal.

For the avoidance of doubt, by a catalyst which comprises activated carbon, alumina and/or an oxide of a transition metal, we include catalysts that are essentially only activated carbon, alumina and/or an oxide of a transition metal and catalysts that are activated carbon, alumina and/or an oxide of a transition metal modified, for example, by the addition of one or more metals (e.g. transition metals) and/or compounds thereof.

By "activated carbon", we include any carbon with a relatively high surface area such as from about 50 to about 3000 $m^2$ or from about 100 to about 2000 $m^2$ (e.g. from about 200 to about 1500 $m^2$ or about 300 to about 1000 $m^2$). The activated carbon may be derived from any carbonaceous material, such as coal (e.g. charcoal), nutshells (e.g. coconut) and wood. Any form of activated carbon may be used, such as powdered, granulated and pelleted activated. Activated carbon which has been modified (e.g. impregnated) by the addition of Cr, Mn, Au, Fe, Sn, Ta, Ti, Sb, Al, Co, Ni, Mo, Ru, Rh, Pd and/or Pt and/or a compound (e.g. a halide) of one or more of these metals may be used.

Alumina which has been modified by the addition of Cr, Mn, Fe, Sn, Ta, Ti, Sb, Al, Co, Ni, Mo, Ru, Rh, Pd and/or Pt and/or a compound (e.g. a halide) of one or more of these metals may be used.

An oxide of a transition metal that has been modified by the addition of Cr, Mn, Au, Fe, Sn, Ta, Ti, Sb, Al, Co, Ni, Mo, Ru, Rh, Pd and/or Pt and/or a compound (e.g. a halide) of one or more of these metals may be used.

A preferred oxide of a transition metal is an oxide of Cr, Ti, V, Zr, or Fe. For example, chromia ($Cr_2O_3$) alone, or chromia that has been modified by the addition of Zn, Mn, Zr, Ni, Al and/or Mg and/or a compound of one or more of these metals may be used. Suitable chromia-based catalysts include those described in EP-A-0502605, EP-A-0773061, EP-A-957074, WO 98/10862 and WO 2006/106353. A preferred chromia-based catalyst is a zinc/chromia catalyst.

Activated carbon is currently a preferred catalyst for step (iii) because, for example, it is cheap, effective and robust. Activated carbon is commercially available, e.g. from Sutcliffe-Speakman.

Step (iii) may be conducted in the vapour or liquid phase, preferably in the vapour phase. Step (iii) may be carried in the liquid phase using the 243db product as the solvent. The heat of reaction in such a process may be removed by boiling off the 243db product/solvent.

Typically, step (iii) is conducted at a temperature of from about −100 to about 400° C., such as from about −80 to about 300° C. or −50 to about 250° C., e.g. from about 0 to about 200° C. or about 50 to about 150° C. The process may be conducted at a pressure of from about 0 to about 30 bara, such as from about 0.1 to about 20 bara or from about 0.5 to about 10 bara, e.g. from about 1 to about 5 bara.

Step (iii) can be carried out in any suitable apparatus, such as a static mixer, a tubular reactor, a stirred tank reactor or a stirred vapour-liquid disengagement vessel. Step (iii) may be carried out batch-wise or continuously.

The reaction time for step (iii) generally is from about 1 second to about 100 hours, preferably from about 10 seconds to about 50 hours, such as from about 1 minute to about 10 hours.

Typically, the molar ratio of 1243zf:compound of formula AB (e.g. $Cl_2$) in step (iii) is from about 10:1 to about 1:5, such as from about 5:1 to about 1:2, for example from about 3:1 to about 1.5:1 (e.g. about 2.5:1 to about 1:1).

The compound of formula $CF_3CHACH_2B$ (e.g. 243db) formed in step (iii) may be purified and/or isolated before being used in step (iv). For example, the compound of formula $CF_3CHACH_2B$ may be separated (e.g. by distillation, condensation and phase separation, and/or scrubbing with water or aqueous base) from the compound of formula AB and 1243zf in step (iii) and transferred to a different reaction vessel or zone for conducting the fluorination step (iv).

In this way, the reaction conditions (e.g. temperature and pressure) used in step (iii) and (iv) can be optimised to facilitate the halogenation and fluorination reactions, respectively. For example, it is currently thought to be optimal to use higher temperature and/or pressure conditions in the fluorination step (iv) compared to the halogenation step (iii).

In another embodiment, step (iii) may be combined with step (iv), i.e. these steps may be carried out simultaneously in a one-pot process. This combined process (referred to hereinafter as process (x)) comprises contacting 3,3,3-trifluoropropene (1243zf) with a compound of formula AB selected from $Cl_2$, $Br_2$, $I_2$, ClF, ClBr, and ICl and HF in the presence of a zinc/chromia catalyst to produce a compound of formula $CF_3CHFCH_2X$, wherein X is Cl or F. Thus, in process (x), the zinc/chromia catalyst acts as both a chlorination and fluorination catalyst. Chlorine ($Cl_2$) is a preferred compound of formula AB in process (x).

In process (x), the conditions used (e.g. temperature, pressure and molar ratio of 1243:chlorine) fall within the broadest ranges set out above in relation to the halogenation of 1243zf to the compound of formula $CF_3CHACH_2B$ (e.g. 243db) (i.e. step (iii) alone). However, the simultaneous chlorination/hydrofluorination in process (x) may require a higher temperature compared to the corresponding halogenation (e.g. chlorination) alone defined in step (iii). For example, preferred temperature conditions for process (x) typically range from about 50 to about 400° C., such as from about 100 to about 350° C.

Typically, HF will be used in a molar excess compared to the amount of 1243zf and/or chlorine in process (x). For example, the molar ratio of HF:1243zf may be in the range of from about 1:1 to about 200:1, such as from about 2:1 to about 150:1, e.g. from about 5:1 to about 100:1.

As described hereinbefore, steps (a) and (b) may be conducted in a one-pot process. Steps (a) and (b) correspond to steps (iv) and (v). Thus, steps (iii), (iv) and (v) may also be carried out simultaneously, and in a further aspect of the invention, there is provided a process for preparing 1234yf comprising contacting 3,3,3-trifluoropropene (1243zf) with chlorine a compound of formula AB and HF in the presence of a zinc/chromia catalyst to produce 1234yf, wherein A and B represent, independently, H, F, Cl, Br or I, provided that A and B are not both H or F. This will be referred to hereinafter as process (y).

Any suitable halogenating agent of formula AB may be used in process (y). Examples include $Cl_2$, $Br_2$, $I_2$, ClF, ClBr, and ICl. Preferably, at least one of A or B is Cl and, therefore, 1243zf is chlorinated by contacting it with $Cl_2$, ClF, ClBr and/or ICl. Chlorine ($Cl_2$) is a preferred chlorinating agent.

In this process, the zinc/chromia catalyst acts as a chlorination, fluorination and dehydrohalogenation catalyst.

Process (y) may be carried out in the liquid or vapour phase and at a temperature of from about −100 to about 400° C., such as from about 0 to about 390° C. or about 100 to about 350° C., e.g. about 150 to about 300° C. A pressure of from 0 to about 30 bara may be used in process (y), such as from about 0.1 to about 25 bara or about 0.5 to about 20 bara, e.g. from about 1 to about 20 bara.

Typically, the molar ratio of 1243zf:compound of formula AB (e.g. $Cl_2$) in process (y) is from about 10:1 to about 1:5, such as from about 5:1 to about 1:2, for example from about 3:1 to about 1.5:1 (e.g. about 2.5:1 to about 1:1). The molar ratio of HF:organics is typically in the range of from about 0.1:1 to about 100:1, such as from about 0.5:1 to about 50:1 or about 1:1 to about 40:1, e.g. from about 2:1 to about 30:1 or from about 5:1 to about 20:1.

Typically, the 1234yf formed in process (y) is purified. This may be achieved by conventional methods, such as by distillation, condensation, phase separation and/or scrubbing (e.g. with water or aqueous base).

In a further embodiment, the subject invention provides a process for preparing 3,3,3-trifluoropropene (1243zf), the process comprising contacting a compound of formula $CX_3CH_2CH_2X$ or $CX_3CH=CH_2$, with hydrogen fluoride (HF) in the presence of a zinc/chromia catalyst, wherein each X independently is F, Cl, Br or I, provided that in the compound of formula $CX_3CH=CH_2$, at least one X is not F. Unless otherwise stated, this will be referred to hereinafter as the 1243zf preparation process (of the invention).

In a preferred embodiment, this process relates to the reaction of a compound of formula $CX_3CH_2CH_2X$ to produce 1243zf.

The compound of formula $CX_3CH_2CH_2X$ represents any halopropane wherein X=F, Cl, Br or I. In a preferred aspect, X=F or Cl. Examples of compounds of formula $CX_3CH_2CH_2X$ include 1,1,1,3-tetrachloropropane ($CCl_3CH_2CH_2Cl$, 250fb), 1,1,3-trichloro-1-fluoropropane ($CCl_2FCH_2CH_2Cl$), 1,3-dichloro-1,1-difluoropropane ($CClF_2CH_2CH_2Cl$), 3-chloro-1,1,1-trifluoropropane ($CF_3CH_2CH_2Cl$, 253fb) and 1,1,1,3-tetrafluoropropane ($CF_3CH_2CH_2F$, 254fb).

In one aspect, the compound of formula $CX_3CH_2CH_2X$ is selected from 250fb, 253fb and 254fb. In a preferred embodiment, the compound of formula $CX_3CH_2CH_2X$ is 253fb. In a further preferred embodiment, the compound of formula $CX_3CH_2CH_2X$ is 254fb. In a particularly preferred embodiment, the compound of formula $CX_3CH_2CH_2X$ is 250fb.

The compound of formula $CX_3CH=CH_2$ represents any halopropene wherein X=F, Cl, Br or I, provided that at least one X is not F. Preferably, X is F or Cl (provided that at least one X is not F). Examples of compounds of formula $CX_3CH=CH_2$ include 3,3,3-trichloropropene ($CCl_3CH=CH_2$), 3,3-dichloro-3-fluoropropene ($CCl_2FCH=CH_2$) and 3-chloro-3,3-difluoropropene ($CClF_2CH=CH_2$). In a preferred aspect, the compound of formula $CX_3CH=CH_2$ represents 3,3,3-trichloropropene.

The inventors have unexpectedly found that zinc/chromia catalysts are particularly effective for the fluorination and/or dehydrohalogenation reactions required by the 1243zf preparation process. In particular, the zinc/chromia catalysts are believed to be more active than other catalysts, such as chromia-based catalysts. This enables the 1243zf preparation process to be conducted using less forcing conditions (e.g. lower temperature and/or pressure) than would otherwise be necessary.

The zinc/chromia catalyst may be used in the 1243zf preparation process in an amount of from about 0.01 to about 50% by weight, such as from about 0.1 to about 30%, for example from about 0.5 to about 20%, based on the combined weight of organics (e.g. compound of formula $CX_3CH_2CH_2X$ or $CX_3CH=CH_2$) and HF.

The 1243zf preparation process can be carried out in any suitable apparatus, such as a static mixer, a stirred tank reactor or a stirred vapour-liquid disengagement vessel. Preferably, the apparatus is made from one or more materials that are resistant to corrosion, e.g. Hastelloy® or Inconel®.

The 1243zf preparation process may be carried out batchwise or (semi-)continuously. Preferably, the process of the invention is carried out continuously. Typically, the 1243zf preparation process is carried out in the vapour phase.

The process may be carried out at atmospheric, sub- or super atmospheric pressure, typically at from 0 to about 30 bara, preferably from about 1 to about 20 bara.

Typically, the 1243zf preparation process of the invention is carried out a temperature of from about 100° C. to about 500° C. (e.g. from about 150° C. to about 500° C. or about 100 to about 450° C.). Preferably, the process is conducted at a temperature of from about 150° C. to about 450° C., such as from about 150° C. to about 400° C., e.g. from about 200° C. to about 350° C. Lower temperatures may also be used in the process of the invention, for example in the conversion of 250fb to 1243zf, such as from about 150° C. to about 350° C., e.g. from about 150° C. to about 300° C. or from about 150° C. to about 250° C.

The 1243zf preparation process typically employs a molar ratio of HF:organics of from about 1:1 to about 100:1, such as from about 3:1 to about 50:1, e.g. from about 4:1 to about 30:1 or about 5:1 or 6:1 to about 20:1 or 30:1.

The reaction time for the 1243zf preparation process generally is from about 1 second to about 100 hours, preferably from about 10 seconds to about 50 hours, such as from about 1 minute to about 10 or 20 hours. In a continuous process, typical contact times of the catalyst with the reagents is from about 1 to about 1000 seconds, such from about 1 to about 500 seconds or about 1 to about 300 seconds or about 1 to about 50, 100 or 200 seconds.

The 1243zf preparation process is particularly effective for preparing 3,3,3-trifluoropropene (1243zf) by contacting 1,1,1,3-tetrachloropropane (250fb) with hydrogen fluoride (HF) in the presence of a zinc/chromia catalyst.

250fb may be purchased from common suppliers of halogenated hydrocarbons, such as Apollo Scientific, Stockport, UK. Alternatively, 250fb may be prepared by the telomerisation of carbon tetrachloride ($CCl_4$) and ethylene (see, for example, J. Am. Chem. Soc. Vol. 70, p 2529, 1948, which is incorporated herein by reference).

The conversion of 250fb to 1243zf typically involves fluorination and dehydrohalogenation sub-steps.

For example, 250fb may be fluorinated to produce a compound of formula $CX_3CH_2CH_2Cl$ (wherein X=Cl or F), as illustrated in the scheme below. 1243zf may be produced by a final dehydrochlorination step of the compound of formula $CX_3CH_2CH_2Cl$ wherein X=F. This is illustrated below as route (a).

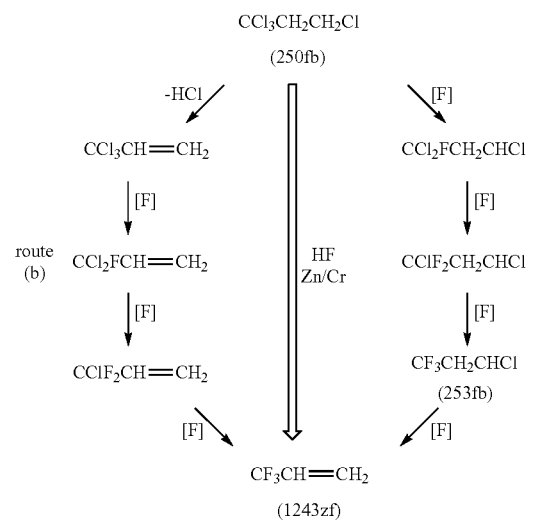

Alternatively, 250fb may be dehydrochlorinated to produce 3,3,3-trichloropropene, followed by step-wise fluorination to produce 1243zf. This is illustrated above as route (b). Routes (a) and (b) correspond to routes (ii1) and (ii2), respectively, as described herein in relation to step (ii) of the process of the invention.

Either or both routes (a) and (b) may be operable to convert 250fb to 1243zf. For example, $CCl_2FCH_2CHCl$ in route (a) may be dehydrochlorinated to produce $CCl_2FCH=CH_2$ in route (b). It is anticipated that some of these reactions may occur spontaneously if HF and 250fb are mixed at elevated temperatures, but the reaction will not go to completion in the absence of a zinc/chromia catalyst in any reasonable timescale.

Surprisingly, the inventors have found that zinc/chromia catalysts are effective at facilitating the one-pot conversion of 250fb and HF to 1243zf. In particular, the activity of the catalyst is believed to allow less forcing conditions (e.g. lower temperatures) compared to known (vapour phase) processes for producing 1243zf, whilst maintaining excellent conversion of 250fb and selectivity to 1243zf.

The invention will now be illustrated by the following non-limiting examples.

EXAMPLE 1

Single Stage Dehydrohalogenation of $CF_3CFHCH_2F$ (245eb) to 1234yf

A 1.25 cm (0.5")×30 cm Inconel reactor tube loaded with 4 g 5.2% zinc/chromia catalyst. The catalyst was dried under flowing nitrogen (50 ml/min) for 2 hours at 250° C. After the drying time, HF (5-8 ml/min) was introduced into the nitrogen stream to begin fluorination of the catalyst. The temperature was ramped to 380° C. at 40° C./min and held there for 16 hours. After 2-3 hours HF breakthrough was detected in the reactor off-gas and the nitrogen flow was switched off. After this treatment the reactor temperature was reduced to the temperatures shown in Table 1 and a mixture comprising nitrogen and 245eb passed over it. Samples of the reactor off-gas were taken and analysed by GC and GC-MS. The GC was calibrated using known standards to determine response factors and an average response factor was used to quantify unknowns.

TABLE 1

| Nitrogen flow 8 ml/min, 245eb flow 2 ml/min | | | | | | | | | |
|---|---|---|---|---|---|---|---|---|---|
| | Temperature ° C. | | | | | | | | |
| Product | 200 | 225 | 250 | 275 | 300 | 325 | 350 | 375 | 400 |
| 1234yf | 0.4 | 0.9 | 2.4 | 17.7 | 40.7 | 51.8 | 88.8 | 96.4 | 100.0 |
| 1243zf | 0.1 | 0.2 | 0.0 | 0.0 | 0.0 | 0.0 | 0.0 | 0.0 | 0.0 |
| 245eb | 99.2 | 97.2 | 93.2 | 71.2 | 59.2 | 48.2 | 2.9 | 0.0 | 0.0 |
| 245cb | 0.2 | 1.7 | 4.3 | 11.1 | 0.0 | 0.0 | 8.2 | 3.6 | 0.0 |

245cb = $CF_3CF_2CH_3$

The results in Table 1 show that zinc/chromia is a surprisingly effective catalyst for the dehydrofluorination of 245eb to 1234yf.

EXAMPLE 2

Preparation of 1234yf/245eb from 243db

Two Inconel reactors (30 cm×0.5") were loaded with 6 g each of a 5.2% Zn/chromia catalyst. These tubes were then places in series and the catalyst dried under flowing nitrogen (80 ml/min) at 250° C. and 3 barg pressure overnight. The catalyst was then activated by treatment with a mixture of 4 ml/min HF and 80 ml/min nitrogen at 300° C. and 3 barg pressure for a period of 72 hours. Whilst at 300° C. the nitrogen flow was reduced to zero. When HF breakthrough was detected (4 hours), the temperature was ramped to 380° C. at 25° C./hour and held there for a further 7 hours.

After activation the pressure was increased to 15 barg and the first reactor temperature was set to 340° C. and the second set to 100° C. and a feed mixture consisting of 243db (10 ml/min) and HF (100 ml/min) passed through them. The gases exiting the train of reactors were sampled and analysed by GC-MS, the results are presented below:

243db conversion 90

Products: 1233xf (70%), 244 isomers including $CF_3CFClCH_3$ (10%), 1234yf (1.4%), 245eb (1.0%)

EXAMPLE 3

Hydrofluorination of 250fb ($CCl_3CH_2CH_2Cl$) at Elevated Pressure

The reactor, made from an Inconnel tube 30 cm×0.5 inches, was charged with 6 g of a 5.2% Zn/Chromia catalyst which was essentially amorphous in character, which was treated as follows:

The catalyst was first dried by heating under nitrogen (80 ml/min) at 250° C. and 3 barg for 48 hours. Next, pre-fluorination of the catalyst was begun by introducing HF (4 ml/min) into the nitrogen stream and increasing the temperature to 300° C. for 16 hours. During the last 5 hours the nitrogen flow was reduced steadily to zero. The temperature was then ramped to 380° C. at 25° C./hr and held at 380° C. for 7 hours and then cooled to 250° C. at 25° C./hr.

A feed mixture comprising 250fb (3 ml/min) and HF (45 ml/min) was then passed over the catalyst at 15 barg and 200° C. The gases exiting the reactor were periodically sampled and analysed by GC after passing through an alkaline scrubber to remove acid gases. The only products detected in the reactor off-gases following removal of the acid gases were the desired product 1243zf (91 mol %, $CF_3CH=CH_2$) and 1,1-difluoro-1,3-dichloropropane (9 mol %, $CF_2ClCH_2CH_2Cl$).

It is believed that the 1,1-difluoro-1,3-dichloropropane could be converted to 1243zf by altering the reaction conditions (e.g. by increasing the temperature and/or contact time). In this way, 250fb could be fully converted in 100% selectivity to 1243zf in a single pass.

EXAMPLE 4

Hydrofluorination of 250fb ($CCl_3CH_2CH_2Cl$) at Atmospheric Pressure

The reactor, made from an Inconnel tube 30 cm×0.5 inches, was loaded with 2.0 g of a 5.2% wt Zn on chromia catalyst which was essentially amorphous in character. The catalyst was then dried under nitrogen (80 ml/min) at 250° C. for 3 hours. HF (20 ml/min) was then introduced into the nitrogen flow and pre-fluorination of the catalyst commenced. When HF was detected in the reactor off-gases the reactor temperature was ramped from 250° C. to 370° C. at 25° C./hr and maintained there for 7 hours before being cooled back to 200° C. at 25° C./hr.

A feed mixture comprising 250fb (1 ml/min), HF (25 ml/min) and nitrogen (30 ml/min) was fed to the reactor at 200° C. for a total of 15 hours. The gases exiting the reactor were scrubbed with a an alkaline solution to remove acid gases and analysed by GC-MS and GC. The only species identified in the scrubbed reactor off-gases throughout the whole experiment was 1243zf.

Examples 3 and 4 demonstrate that the reaction of 250fb with HF using a zinc/chromia catalyst selectively produces 1243zf under very mild conditions.

EXAMPLE 5

Vapour Phase Conversion of 254fb ($CF_3CH_2CH_2F$) to 1243zf ($CF_3CH=CH_2$)

The reactor, made from an Inconnel tube 30 cm×0.5 inches was loaded with 2.0 g of a 5.2% wt Zn on chromia catalyst which was essentially amorphous in character. The catalyst was then dried under nitrogen (80 ml/min) at 250° C. for 3 hours. HF (20 ml/min) was then introduced into the nitrogen flow and pre-fluorination of the catalyst commenced. When HF was detected in the reactor off-gases the reactor temperature was ramped from 250° C. to 370° C. at 25° C./hr and maintained there for 7 hours before being cooled back to 200° C. at 25° C./hr.

Mixtures of HF and 254fb were then fed across the catalyst at various temperatures and ratio's to demonstrate the conversion of 254fb to 1243zf. Nitrogen carrier gas flows were used to aid delivery of the feeds to the reactor. The gases exiting the reactor were analysed by GC-MS and GC. The results are summarised in the Table below:

| Temperature (° C.) | 200 | 225 | 250 | 200 | 225 | 250 | 275 | 300 | 300 | 225 | 250 |
|---|---|---|---|---|---|---|---|---|---|---|---|
| 254fb feed (ml/min) | 13.5 | 12.1 | 16.7 | 20.4 | 22.9 | 10.6 | 12.8 | 10.0 | 1.0 | 4.9 | 4.9 |
| HF feed (ml/min) | 27.9 | 27.9 | 27.6 | 34.3 | 35.3 | 35.4 | 35.2 | 35.6 | 35.3 | 0 | 0 |
| Ratio HF:254fb | 2.1 | 2.3 | 1.7 | 1.7 | 1.5 | 3.3 | 2.8 | 3.6 | 35.4 | N/A | N/A |
| Total $N_2$ flow (ml/min) | 10.1 | 10.1 | 10.1 | 10.1 | 10.1 | 10.1 | 10.1 | 10.1 | 10.1 | 5 | 5 |
| ROG* 254fb (mol %) | 93.3 | 50.1 | 14.8 | 93.3 | 71.9 | 17.4 | 1.5 | 0.1 | 0.7 | 1.3 | 0.1 |
| ROG* 1243zf (mol %) | 6.7 | 49.9 | 85.2 | 6.7 | 28.1 | 82.6 | 98.5 | 99.9 | 99.3 | 98.7 | 99.9 |

*ROG = Reactor Off-gas composition

As can be seen the conversion of 254fb to 1243xf is clean and facile over a zinc/chromia catalyst at moderate conditions.

The invention claimed is:

1. A process for the preparation of 2,3,3,3-tetrafluoropropene (1234yf) comprising:
   (a) contacting in the vapor phase at a temperature of from 100 to 400° C. and at super-atmospheric pressure up to 30 bara.1,1,1-trifluoro-2,3-dichloropropane (243db) with hydrogen fluoride (HF) in the presence of a zinc/ chromia catalyst containing from 0.01 to about 25% by weight of zinc or a compound of zinc to produce a compound having the formula $CF_3CHFCH_2X$, wherein X is Cl or F; and (b) dehydrohalogenating the compound of formula $CF_3CHFCH_2X$ to produce 1234yf, said dehydrohalogenating being (i) induced thermally, (ii) base-mediated, or (iii) catalyzed by a catalyst selected form a carbon-based catalyst, a catalyst comprising a main group metal, or a catalyst comprising a transition metal.

2. A process according to claim 1 wherein step (a) is carried out at in the vapour phase a temperature of from 100 to 380° C. and a super-atmospheric pressure of from up to 28 bara.

3. A process according to claim 1 wherein step (b) is carried out at in the vapour and/or liquid phase a temperature of from −70 to 1000° C. and a pressure of from 0 to 30 bara.

4. A process according to claim 1 wherein step (b) is carried out in the presence of a catalyst selected from the group consisting of: zinc/chromia catalyst, a crown ether, including 18-crown-6, a quaternary ammonium salt, fluorinated catalysts, and mixtures thereof.

5. A process according to claim 4 wherein step (b) is carried out at a temperature of from −70 to 400° C.

6. A process according to claim 1 wherein step (a) is carried out at a pressure of from 5 to 28 bara.

7. A process according to claim 1 wherein step (b) is carried out at a pressure of from 0.1 to 20 bara.

8. A process according to claim 1 wherein step (b) is carried out in the presence of HF.

9. A process according to claim 1 wherein step (b) is carried out in the absence of an added HF feed.

10. A process according to claim 1 wherein step (b) is carried out in the presence of a diluent gas.

11. A process according to claim 1 wherein the molar ratio of HF:organics in step (a) is from 1:1 to 100:1.

12. A process according to claim 1 wherein the molar ratio of HF:organics in step (b) is from 0.01:1 to 50:1.

13. A process according to claim 1 wherein step (b) is carried out in the presence of a base.

14. A process according to claim 13 wherein step (b) is carried out at a temperature of from −50 to 300° C.

15. A process according to claim 13 wherein the base is selected from a metal hydroxide, including alkali metal hydroxides, sodium hydroxide and potassium hydroxide, an alkaline earth metal hydroxide, including calcium hydroxide, metal amide and mixtures thereof.

16. A process according to claim 13 wherein step (b) is carried out in a solvent.

17. A process according to claim 16 wherein the solvent is selected from water, alcohols, diols, polyols, polar aprotic solvents and mixtures thereof.

18. A process according to claim 17 and wherein the process optionally is carried out in the presence of a co-solvent or diluent.

19. A process according to 1 comprising the step (iii) of contacting 3,3,3-trifluoropropene (1243zf) with a compound of formula AB to produce a compound of formula $CF_3CHACH_2B$ wherein A and B represent, independently, H, F, Cl, Br or I, provided that A and B are not both H or F.

20. A process according to claim 19 comprising the step (ii) of converting 1,1,1,3-tetrachloropropane (250fb) to 3,3,3-trifluoropropene (1243zf).

21. A process according to claim 20 comprising the step (i) of telomerising ethylene and carbon tetrachloride ($CCl_4$) to produce the 1,1,1,3-tetrachloropropane.

22. A process according to claim 19 wherein the compound of formula AB is $Cl_2$ and the compound of formula $CF_3CHACH_2B$ is 1,1,1-trifluoro-2,3-dichloropropane (243db).

* * * * *

UNITED STATES PATENT AND TRADEMARK OFFICE
CERTIFICATE OF CORRECTION

PATENT NO. : 8,552,228 B2  Page 1 of 1
APPLICATION NO. : 12/736445
DATED : October 8, 2013
INVENTOR(S) : Smith et al.

It is certified that error appears in the above-identified patent and that said Letters Patent is hereby corrected as shown below:

Title Page:
Item (73) Assignee: delete "Mexichem Amanco Holdings S.A. de C.V." and substitute
-- Mexichem Amanco Holding, S.A. de C.V. --

In the Claims:
Column 22, line one of claim 19, after "according to" insert -- claim --

Signed and Sealed this
Seventeenth Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,552,228 B2  Page 1 of 1
APPLICATION NO. : 12/736445
DATED : October 8, 2013
INVENTOR(S) : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this
Fifteenth Day of September, 2015

Michelle K. Lee
*Director of the United States Patent and Trademark Office*